(12) United States Patent
Mascotto et al.

(10) Patent No.: US 12,381,568 B2
(45) Date of Patent: Aug. 5, 2025

(54) SIGNAL PROCESSING CIRCUIT AND SIGNAL PROCESSING DEVICE

(71) Applicant: ams Sensors Germany GmbH, Jena (DE)

(72) Inventors: Massimo Mascotto, Milan (IT); Dalibor Stojkovic, Erfurt (DE); Steffen Fritzlar, Erfurt (DE)

(73) Assignee: AMS SENSORS GERMANY GMBH, Jena (DE)

( * ) Notice: Subject to any disclaimer, the term of this patent is extended or adjusted under 35 U.S.C. 154(b) by 184 days.

(21) Appl. No.: 18/279,498

(22) PCT Filed: Feb. 21, 2022

(86) PCT No.: PCT/EP2022/054252
§ 371 (c)(1),
(2) Date: Aug. 30, 2023

(87) PCT Pub. No.: WO2022/184488
PCT Pub. Date: Sep. 9, 2022

(65) Prior Publication Data
US 2024/0154619 A1    May 9, 2024

(30) Foreign Application Priority Data
Mar. 2, 2021  (DE) ............ 10 2021 104 980.6

(51) Int. Cl.
*H03M 1/12* (2006.01)
*H03M 1/08* (2006.01)

(52) U.S. Cl.
CPC ............. *H03M 1/125* (2013.01); *H03M 1/08* (2013.01); *H03M 1/123* (2013.01)

(58) Field of Classification Search
CPC .... H03M 1/12; H03M 1/1205; H03M 1/0617; H03M 1/0624; H03M 1/1009;
(Continued)

(56) References Cited

U.S. PATENT DOCUMENTS 5,289,191 A     2/1994  Elms
6,313,637 B1 *  11/2001 Iino ................. H02J 7/0048
                                                  324/434
(Continued)

FOREIGN PATENT DOCUMENTS

CN       104783776 B       2/2018
DE    11 2018 000 383 T5  10/2019

OTHER PUBLICATIONS

International Search Report issued on May 18, 2022, for corresponding International Patent Application No. PCT/EP2022/054252 (4 pages).
(Continued)

*Primary Examiner* — Linh V Nguyen
(74) *Attorney, Agent, or Firm* — HAUPTMAN HAM, LLP

(57) ABSTRACT

A signal processing circuit includes a first current sensor input, a second current sensor input, a voltage sensor input for receiving a sensor voltage, a first selection unit, a second selection unit, a current analog-digital converter (ADC), a voltage ADC, digital processing block, and a current-voltage converter. The first selection unit includes a first current input coupled to the first current sensor input, and a second current input coupled to the second current sensor input. The second selection unit includes a first voltage input coupled to the voltage sensor input and a second voltage input. The current ADC is coupled to a first current output. The voltage ADC is coupled to a voltage output. The digital processing block is coupled to outputs of the current ADC and the voltage ADC. The current-voltage converter is coupled between a second current output and the second voltage input.

11 Claims, 3 Drawing Sheets

(58) Field of Classification Search
CPC ........ H03M 1/123; H03M 1/125; H03M 1/34;
H03M 1/38; H03M 1/468; G01R
31/3842; G01R 31/396; G01R 31/389;
G01R 31/392; G01R 19/16542; G01R
27/02; G01R 31/2841; G01R 31/31924;
G01R 31/374; G01R 19/25; G01R
19/2513; G01R 21/133; G01R 27/2605;
G01R 31/002; G01R 31/088; G01R
31/2874; G01R 31/2879; G01R 31/3004;
G01R 31/3163; G01R 31/3167; G01R
31/31725; G01R 31/31926; G01R
31/3648; G01R 31/367; G01R 31/3835;
G01R 31/52; G01R 35/00; A61B 5/318;
A61B 5/053; A61B 5/0537; A61B
5/4519; A61B 5/486; A61B 5/684; A61B
5/6843; A61B 18/00; A61B 5/14551
USPC .................. 341/116, 117, 141, 142, 155
See application file for complete search history.

(56) References Cited

U.S. PATENT DOCUMENTS

| | | | | |
|---|---|---|---|---|
| 9,999,397 | B2* | 6/2018 | Lee ................... | A61B 5/7225 |
| 2006/0290556 | A1* | 12/2006 | Sherry ................ | H03M 1/0624 |
| | | | | 341/156 |
| 2009/0121908 | A1* | 5/2009 | Regier ............... | G01R 31/3163 |
| | | | | 341/142 |
| 2009/0273498 | A1* | 11/2009 | Goder ................ | H02M 3/1584 |
| | | | | 341/141 |
| 2010/0321227 | A1 | 12/2010 | Hales et al. | |
| 2012/0004699 | A1* | 1/2012 | Bobgan ............... | A61N 1/3706 |
| | | | | 607/27 |
| 2013/0338473 | A1* | 12/2013 | Bohorquez .......... | A61B 5/053 |
| | | | | 600/393 |
| 2017/0055845 | A1 | 3/2017 | Mirov et al. | |
| 2021/0223327 | A1* | 7/2021 | Berger ................ | G01R 31/396 |
| 2022/0120817 | A1* | 4/2022 | Okada ................ | H01M 10/48 |
| 2023/0083815 | A1* | 3/2023 | Labbe ................. | A61N 1/3704 |
| | | | | 341/118 |
| 2023/0175867 | A1* | 6/2023 | O'Neil ............... | G01D 5/20 |
| | | | | 324/207.11 |
| 2023/0184847 | A1* | 6/2023 | Lin .................... | H02J 7/0047 |
| 2024/0348259 | A1* | 10/2024 | Furuta ................ | H03M 1/123 |

OTHER PUBLICATIONS

Written Opinion issued on May 18, 2022, for corresponding International Patent Application No. PCT/EP2022/054252 (6 pages).
Ajit Sharma et al., "A Sub-60-uA Multimodal Smart Biosensing SoC With > 80-dB SNR, 35-uA Photoplethysmography Signal Chain", IEEE Journal of Solid-State Circuits, Apr. 1, 2017, vol. 52, No. 4, pp. 1021-1033.
Qiuyang Lin et al., "Wearable Multiple Modality Bio-Signal Recording and Processing on Chip: A Review", IEEE Sensors Journal, Aug. 12, 2020, vol. 21, No. 2, pp. 1108-1123.
"AFE4950 Ultra-Small, Integrated AFE for Wearable Optical Heart-Rate Monitoring, SpO2 and Electrical Bio-sensing," Texas Instruments (https://www.ti.com/lit/ds/symlink/afe4950.pdf?ts=1606137786973&ref_url=https%253A%252F%252Fww), Jun. 2020, 8 pages.
MAX86140/MAX86141, "Best-in-Class Optical Pulse Oximeter and Heart-Rate Sensor for Wearable Health", maxim integrated (https://datasheets.maximintegrated.com/en/ds/), 90 pages.

* cited by examiner

SIGNAL PROCESSING CIRCUIT AND SIGNAL PROCESSING DEVICE

CROSS REFERENCE TO RELATED APPLICATION

This application is a National Stage of International Application No. PCT/EP2022/054252, filed on Feb. 21, 2022, which designates the United States and was published in Europe, and which claims priority to German Patent Application No. 10 2021 104 980.6, filed on Mar. 2, 2021, in the German Patent Office. Both of the aforementioned applications are hereby incorporated by reference in their entireties.

The present disclosure relates to a signal processing circuit and to a signal processing device with such a signal processing circuit.

BACKGROUND OF THE INVENTION

Various sensors provide either a voltage signal or a current signal as respective sensor signals. For processing such sensor signals in the digital domain, it is desired to provide analog-to-digital converters, ADCs, adapted to the type of sensor signal, i.e. voltage signals or current signals.

For example, sensors for photoplethysmography, PPG, usually provide current signals, while electrocardiogram, ECG, measurements are performed on a voltage basis. To this end conventional signal processing for such applications provides one ADC for processing said PPG signal and another ADC for processing the ECG signal. If another current-based sensor signal is to be processed, the ADC for PPG has to be shared or another current based ADC has to be provided.

SUMMARY OF THE INVENTION

The present disclosure provides an improved processing concept for processing current based and voltage based sensor signals.

The improved processing concept is based on the idea to process two current-based sensors signals in parallel, e.g. simultaneously, without providing a dedicated second current-based ADC. Instead, one of the current sensor signals is converted into the voltage domain and a voltage based ADC, which is regularly provided for processing a voltage-based sensor signal, is used for processing said signal. To this end a first selection unit is provided for selecting and routing two current sensor signals to the respective ADCs. Furthermore, a second selection unit is provided for selecting whether the voltage-based sensor signal or the current signal being converted into the voltage domain is to be routed to the voltage-based ADC. The outputs of the two ADCs can be processed in a common digital processing block.

For example, a signal processing circuit according to the improved processing concept comprises a first current sensor input for receiving a first sensor current, a second current sensor input for receiving a second sensor current and a voltage sensor input for receiving a sensor voltage. A first selection unit comprises a first current input, which is coupled to the first current sensor input, and a second current input, which is coupled to the second current sensor input. The first selection unit is configured to, based on a first selection signal, select one of the first and the second current input as a first selected input to be connected to a first current output, and to select one, e.g. another one, of the first and the second current input as a second selected input to be connected to a second current output.

A second selection unit comprises a first voltage input, a second voltage input and a voltage output. The first voltage input is coupled to the voltage sensor input. The second selection unit is configured to, based on a second selection signal, connect one of the first and the second voltage input to the voltage output.

The signal processing circuit further comprises a current analog-digital converter, ADC, coupled to the first current output, a voltage ADC coupled to the voltage output and a digital processing block coupled to respective outputs of the current ADC and the voltage ADC. A current-voltage converter is coupled between the second current output of the first selection unit and the second voltage input of the second selection unit.

Such a signal processing circuit allows selectable operation in at least two configurations. For example, in the first configuration one of the current signals received at the first and the second current input is processed with the current ADC while a voltage signal at the voltage sensor input is processed with the voltage ADC, with both digital outputs of the current ADC and the voltage ADC being processed with the digital processing block.

In a second configuration, one of the current sensor signals is processed with the current ADC and the other current sensor signal is processed with the voltage ADC after being converted to a voltage with the current-voltage converter. This allows a flexible operation of the signal processing circuit.

For example, the first selection unit provides two current paths from the first selected input to the first current output and from the second selected input to the second current output. Accordingly, the first selection unit is configured to simultaneously provide respective currents from the first selected input to the first current output and from the second selected input to the second current output. The simultaneously existing current paths allow two current signals to be converted to the digital domain at the same time, such that no time delay occurs between the respective digital current samples.

For example, the signal processing circuit is configured to have photodiodes connected to the first and the second current sensor input. Hence two different photosignals can be processed simultaneously, allowing a combined evaluation of the respective photodiode signals.

In various embodiments at least one of the current ADC and the voltage ADC comprises a delta-sigma modulator. ADCs with delta-sigma modulators, for example, allow the use of noise shaping for improving the respective conversion result.

The current-voltage converter can be implemented with various types of circuits providing such a function. For example, the current-voltage converter comprises a transimpedance amplifier, e.g. featuring an operational amplifier with at least a resistive element in its feedback path.

In some implementations the signal processing circuit further comprises at least one offset current source connected to the first current output or to the second current output. This includes that a separate offset current source is connected to each of the first and the second current output. Accordingly, current offsets in the respective current sensor signals can be compensated for with respective offset currents. In particular, the offset currents are combined with the sensor currents before the analog-to-digital conversion.

In various embodiments the digital processing block comprises a buffer element for buffering digital values provided by the current ADC and the voltage ADC. For example, the buffer element is implemented as a first in, first out, FIFO, element. The values stored in the buffer element may be processed directly in the digital processing block or in a separate processor or other entity connected to the digital processing block. The digital processing block may comprise respective interfaces for this purpose.

The improved processing concept is not limited by exactly two current sensor inputs, which would still be an option, but can also include three or more current sensor inputs. In such implementations the first selection unit can select between any of the available current sensor inputs.

For example, the signal processing circuit further comprises at least one further current sensor input for receiving at least one further sensor current. In such a configuration the first selection unit is configured to, based on the first selection signal, select one of the first, the second and the at least one further current input as the first selected input, and to select one, in particular another one, of the first, the second and the at least one further current input as the second selected input.

While the selection of two different inputs is a reasonable application, it should not be excluded that the same current input can be connected to both the first and the second current output.

Similarly, the second selection unit may comprise further voltage inputs that could be connected either to external voltage inputs or to internal voltage terminals to allow various other measurements.

The signal processing circuit according to one of the implementations described above can, for example, be used in various types of signal processing devices. For example, a signal processing device according to the improved processing concept comprises the signal processing circuit according to one of the embodiments described above, a first photosensitive element connected to the first sensor input, a second photosensitive element connected to the second current sensor input, and a sensor element connected to the voltage sensor input for providing at least one sensor voltage. For example, the photosensitive elements are implemented as one or more photodiodes.

Accordingly, such a signal processing device is able to process either two photosensitive elements in parallel or one of the photosensitive elements together with the sensor element providing the sensor voltage.

For example, the sensor element comprises at least two electrodes for electrocardiogram, ECG, measurement. The signal processing device further comprises a processing block connected between the voltage sensor input and the first voltage input. For example, such a processing block comprises elements for leakage compensation and/or lead-off detection and/or an amplifier for processing the respective voltage signals. Hence, the voltage signal provided to the second selection unit and, if selected, to the voltage ADC, implements an ECG signal to be evaluated.

Accordingly, the signal processing device supports processing of an ECG signal in parallel to one of the photocurrents or as an alternative to one or more photocurrents.

In various implementations the first and the second photosensitive element are adapted for at least one of the following configurations:
the first and the second photosensitive element are configured for photoplethysmography, PPG;
the first photosensitive element is configured for PPG and the second photosensitive element is configured for detection of oxygen saturation;
the first photosensitive element is configured for PPG and the second photosensitive element is configured for ambient light detection.

In the case that both the first and the second photosensitive elements are configured for PPG, for example a multi-wavelength PPG measurement can be performed, improving the quality of the PPG result and/or allowing improved applications.

The configuration where the first photosensitive element is configured for PPG and the second photosensitive element is configured for the detection of oxygen saturation enables parallel measurement and evaluation of both types of measurement signals.

With one photosensitive element being configured for PPG and another one being configured for ambient light detection, the measurement quality of the PPG signal can be improved by incorporating respectively compensating the simultaneously measured ambient light signal, which is included in but deteriorates the PPG measurement.

If, as discussed above, more than two current sensor inputs are available, for example three or four current sensor inputs, respective specifically configured photosensitive elements can be connected to these inputs, allowing selectable configurations, e.g. from one of the configurations described above. In addition, selectable measurement of an ECG signal or other voltage-based signal is still possible.

In various implementations the signal processing device may be implemented as a wearable device, e.g. a smartwatch or a wristband or glasses or the like. The signal processing device may also be implemented as a sensor patch, e.g. with some kind of adhesive to fix the signal processing device to the skin of a person or animal.

BRIEF DESCRIPTION OF THE DRAWINGS

The improved processing concept will be described in more detail in the following with the aid of drawings. Elements having the same or similar function bear the same reference numerals throughout the drawings. Hence their description is not necessarily repeated in following drawings.

In the drawings.

DETAILED DESCRIPTION

Figure 1:
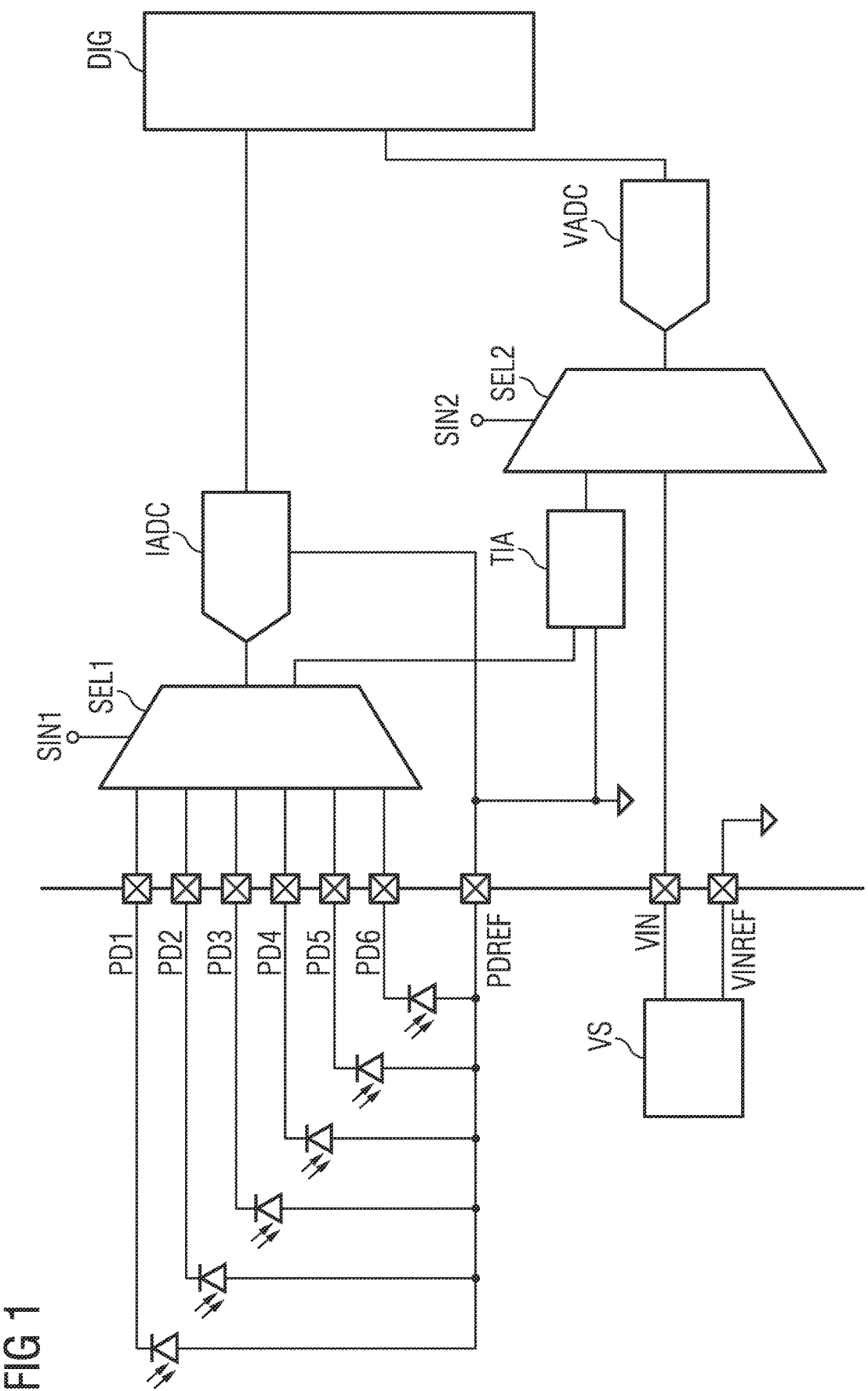
FIG. 1 shows a schematic view of an example signal processing circuit.

FIG. 1 shows an example implementation of a signal processing circuit according to the improved processing concept. The signal processing circuit comprises a first current sensor input PD1, a second current sensor input PD2 and further current sensor inputs PD3, PD4, PD5, PD6. Furthermore, a current reference terminal PDREF can be included that can be connected internally to a reference potential terminal like a ground terminal. A first selection unit SELL has respective current inputs, of which a first current input is connected to the first current sensor input PD1, a second current input is coupled to the second current sensor input PD2 and further current inputs are connected to the further current sensor inputs PD3 to PD6. The first selection unit SELL has a first current output connected to a current ADC IADC and a second current output coupled to a current voltage converter TIA.

The signal processing circuit further comprises a digital processing block DIG that is shown schematically only for reasons of a better overview. For example, an output of the current ADC IADC is coupled to the digital processing block DIG.

The signal processing circuit further comprises a voltage sensor input VIN and a second selection unit SEL2 comprising a first voltage input, which is coupled to the voltage sensor input VIN, and a second voltage input being coupled to an output of the current-voltage converter TIA. A voltage output of the second selection unit SEL2 is coupled to a voltage ADC VADC, which has its output coupled to the digital processing block DIG.

The solid black line including the current sensor inputs PD1 to PD6, the current reference terminal PDREF, the voltage sensor input VIN and the voltage reference terminal VINREF for example resembles a boundary of the signal processing circuit.

FIG. 1 further shows a set of photodiodes as examples for various kinds of photosensitive elements being connected between the respective current sensor inputs PD1 to PD6 and the current reference terminal PDREF. Furthermore, FIG. 1 shows a schematic representation of a sensor element VS connected to a voltage sensor input VIN and the voltage reference terminal VINREF. The photosensitive elements and the sensor element VS may be part of a signal processing device including the signal processing circuit.

The first selection unit SELL is configured to select one of the current inputs, e.g. one of the first and the second current inputs as a first selected input that is to be connected to the first current output and, consequently, to the current ADC IADC. Furthermore, the first selection unit SELL is configured to select one of its current inputs, e.g. the first and the second current input as a second selected input that is to be connected to the second current output and, consequently, to the current-voltage converter TIA. Preferably, the first and the second selected inputs are different from each other.

The selection within the first selection unit SELL is, for example, based on a first selection signal being provided via a first selection input SIN1. For example, the first selection signal is provided from the digital processing block DIG but could also be provided from an entity external to the signal processing circuit.

The second selection unit is configured to connect one of the first and the second voltage input to the voltage output based on a second selection signal that may be provided via a second selection input SIA2. For example, also the second selection signal is provided by the digital processing block DIG but could also be provided from an entity external to the signal processing circuit.

The current-voltage converter TIA is configured to generate a voltage corresponding to the respective input current provided from the first selection unit SEL1. Accordingly, the second selection unit SEL2 provides one of the respective input voltages at its output and to the voltage ADC VADC.

Hence, during operation of the signal processing circuit various configurations for input signals to be processed are available.

For example, in one configuration determined by the respective selection signals one of the currents provided at the current sensor inputs PD1 to PD6, respectively the current inputs of the first selection unit SELL, is provided to the current ADC IADC for converting the current value to a digital representation thereof. The second selection unit SEL2 provides the voltage provided by the sensor element VS to the voltage ADC VADC for generating a digital representation of the respective voltage value. In such a configuration the selection of the second selected input within the first selection unit SELL can be neglected. For example, in such a case even no selection at all is an option, such that no current is provided to the current-voltage converter TIA accordingly.

Eventually, the described configuration allows parallel processing of the selected current sensor input, respectively the selected photosensitive element and the sensor signal of the sensor element VS.

In another configuration, also one of the current inputs, respectively current sensor inputs PD1 to PD6, is selected in the first selection unit SELL as a first selected input, as in the configuration described previously. However, in the present configuration, a second selected input is determined by the first selection signal such that a current provided at the selected input is provided from said selected second input to the current voltage converter TIA for converting it to the corresponding voltage signal. Furthermore, in the second selection unit SEL2, the second voltage input being connected to the output of the current voltage converter TIA is selected via the second selection signal, such that the output voltage of the current voltage converter is provided to the voltage ADC VADC.

Eventually, in this configuration a simultaneous processing of signals from two current sensors, implemented as photosensitive elements in this example, is made possible.

In particular, two parallel current paths are established in the first selection unit SELL between the respective selected inputs and the first and second current outputs. This avoids the need to switch inputs for providing currents over a single current path. Moreover, the parallel provision of the respective sensor currents at the first and the second current output allows simultaneous conversion from the analog to the digital domain via the analog-to-digital converters IADC, VADC which particularly can be beneficial for applications where an exact relationship in time of the respective sensor currents is desired. A sensor voltage from the sensor element VS is neglected in this configuration.

Figure 2:
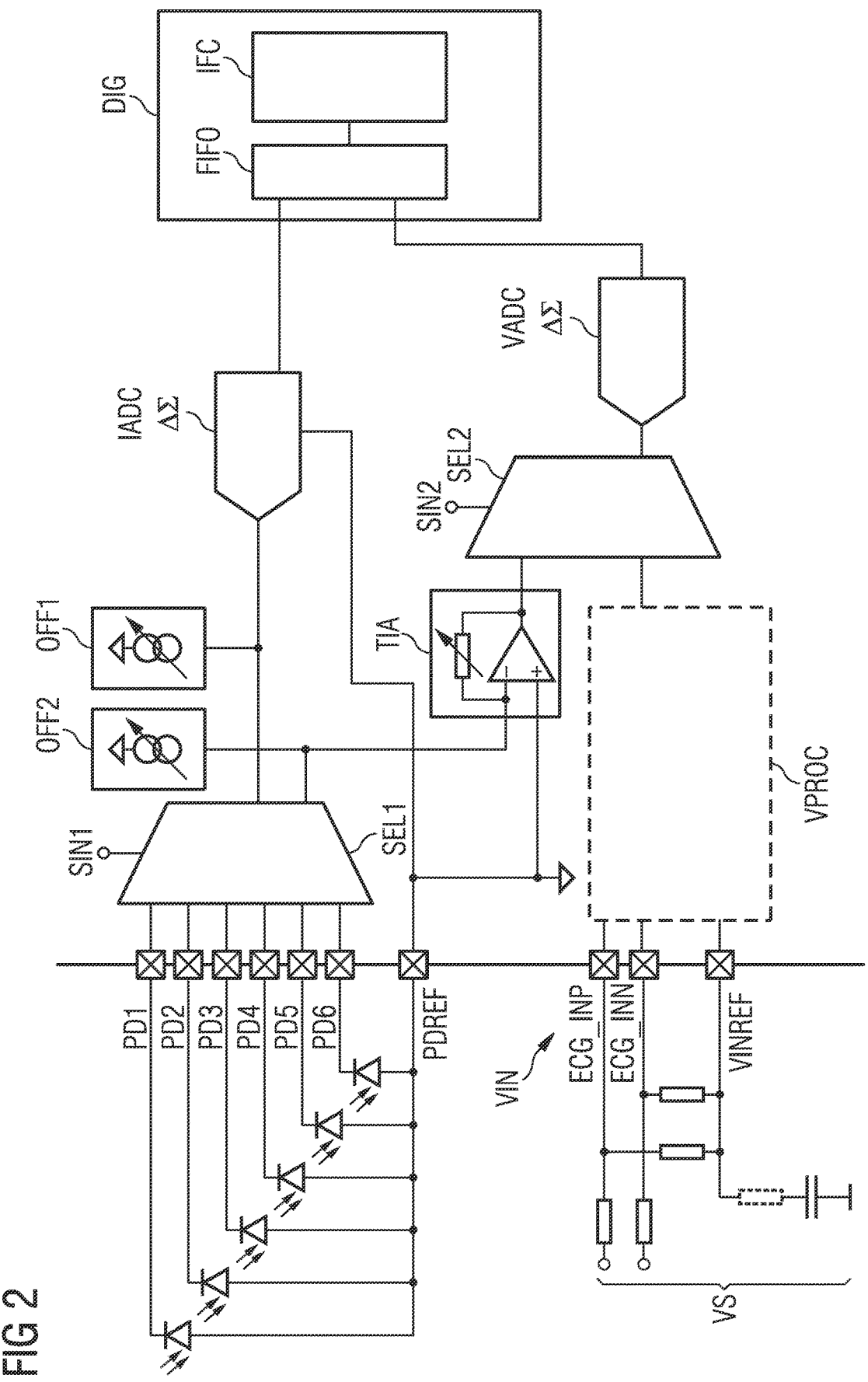
FIG. 2 shows a further schematic view of an example signal processing circuit.

FIG. 2 shows a further schematic view of an example signal processing circuit that is based on the example implementation shown in FIG. 1. Therefore, functions, modes of operation etc. already described in conjunction with FIG. 1 will be omitted in the description of FIG. 2 and differences or extensions will be mainly discussed.

For example, the current ADC IADC and the voltage ADC VADC comprise a delta-sigma modulator that, for example, allows noise shaping of the respective input signal. However, in alternative implementations only one of the ADCs IADC and VADC may be implemented with a delta-sigma modulator based ADC.

Furthermore in the example of FIG. 2, the current-voltage converter TIA is implemented with a transimpedance amplifier. As schematically shown in the respective block, the transimpedance amplifier is implemented with an operational amplifier having a resistive element in its feedback path for the actual current-to-voltage conversion. The feedback path is connected to the inverting input of the operational amplifier that is also connected to the second current output of the first selection unit SEL1. The non-inverting input of the operational amplifier is connected to the reference potential terminal.

Further details could be implemented with the transimpedance amplifier without departing from the schematic approach of a transimpedance amplifier shown in this example. The resistive element in the feedback path may be adjustable, e.g. for tuning an exact ratio between input current and output voltage of the transimpedance amplifier.

In the example implementation of FIG. 2, a first offset current source OFF1 is connected to the first current output and a second offset current source OFF2 is connected to the second current output. This, for example, allows compensation for offset currents comprised in the respective sensor signals, thereby improving signal quality.

The digital processing block DIG may comprise a buffer element for buffering the respective digital values provided by the ADCs IADC and VADC. For example, the buffer element is implemented as a first in, first out, FIFO, buffer allowing, for example, asynchronous processing or forwarding of the buffered values.

Furthermore, the digital processing block DIG may comprise an interface block for providing the buffered values to another device or signal processing circuit or signal processor or the like. For example, the interface block is configured to operate according to the I2C and/or the SPI transmission standard.

In alternative implementations, the digital processing block may also include a digital signal processor for directly processing the buffered digital values.

In the example implementation of FIG. 2, the sensor element VS comprises at least two electrodes for ECG measurement that are coupled to respective electrode terminals ECG_INP, ECG_INN. Furthermore, the sensor element VS is coupled to the voltage reference terminal VINREF. In order to process, respectively preprocess, the signals from the ECG electrodes the signal processing device further comprises a processing block VPROC connected between the voltage sensor input VIN, respectively the electrode terminals ECG_INP, ECG_INN, and the first current input of the second selection unit SEL2. For example, the processing block VPROC comprises circuitry for leakage compensation and/or lead off detection and/or amplification of the respective ECG signals. This may also include circuitry for providing a respective potential to the voltage reference terminal VINREF.

For example, at least two of the photosensitive elements connected at the current sensor inputs PD1 to PD6 are configured for PPG measurement. To this end, the signal processing circuit may also include circuitry for driving respective LEDs as light sources for the PPG measurement. However, for a better overview, such circuitry is not shown in the present schematic representation of FIG. 2.

With reference to the explanation of different possible configurations given in conjunction with FIG. 1, the signal processing circuit of FIG. 2, which has connected respective photosensitive elements configured for PPG measurement, allows selective processing of two PPG channels in parallel, with one channel being processed through the current ADC IADC and the other channel being processed through the transimpedance amplifier and the voltage ADC VADC. This, for example, allows multi-channel PPG processing that may increase PPG quality.

In another configuration, one PPG channel is processed in parallel to the ECG signal.

Figure 3A:
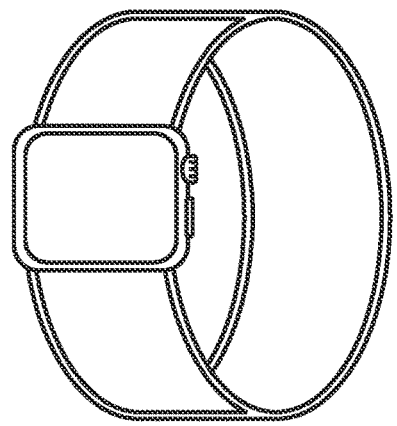
FIGS. 3A-3C show various examples of signal processing devices.
Figure 3B:
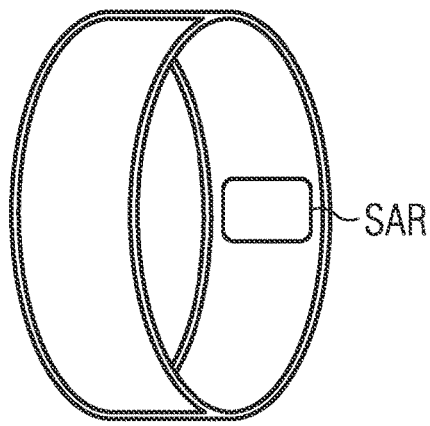
Figure 3C:
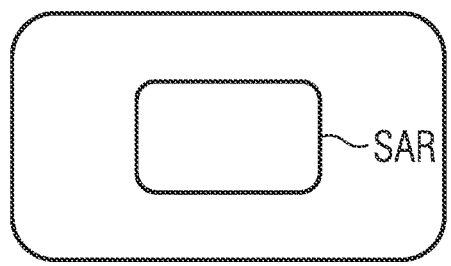

As discussed before, the signal processing circuit together with the respective sensors can form a signal processing device. While an exact implementation of such a signal processing device should not be limited in the following, FIGS. 3A, 3B and 3C show various examples of such signal processing devices. For example, FIGS. 3A and 3B show examples where the signal processing device is implemented as a wearable device like a smartwatch in FIG. 3A and a wristband in FIG. 3B. For example, the wristband comprises a sensor area SAR carrying at least one of the photosensitive elements and/or the voltage sensor element VS, e.g. ECG electrodes. Another implementation, not shown here, is an implementation of the signal processing device as glasses, in particular smart glasses.

FIG. 3C shows the implementation of the signal processing device as a sensor patch where the sensor area SAR is fixed to the skin of a person or animal with some kind of adhesive, such as a band aid.

Despite PPG, one or more of the photosensitive elements connectable to the signal processing circuit can be configured for detection of oxygen saturation, e.g. peripheral oxygen saturation $SpO_2$, and/or ambient light. For example, the ambient light detection can be used to compensate for ambient light effects in the signals from the PPG configured photosensitive elements.

A photosensitive element in the sense of this description may not only be a single photodiode or other single device but may also include groups of such devices that, for example, provide their respective photocurrents in parallel to improve signal quality and/or strength. Hence, several photodiodes or other devices may be arranged in groups that together provide their respective photocurrents to one of the current sensor inputs PD1 to PD6 each.

Figure 4A:
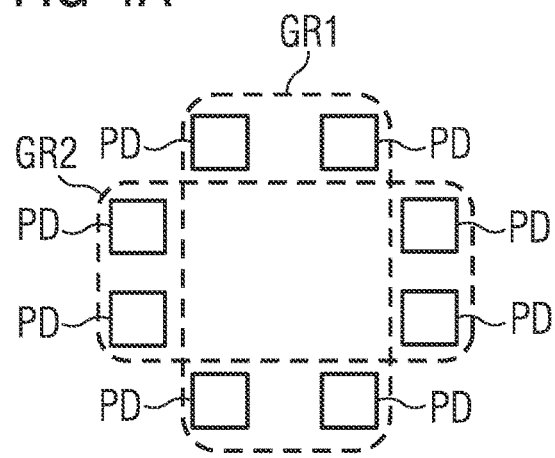
FIGS. 4A and 4B shows example configurations of photosensitive elements.
Figure 4B:
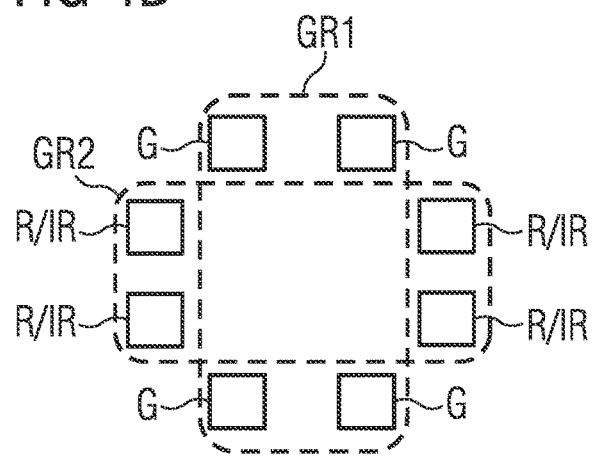

FIG. 4A and FIG. 4B show example configurations of photosensitive elements, in particular photodiodes arranged in groups.

For example, FIG. 4A shows a first group GR1 of photodiodes and a second group GR2 of photodiodes that are arranged in a cross shape in this example. For example, the photodiodes of each group are configured for PPG measurement, such that with the signal processing circuit either one of the groups can be selected that may have a higher signal quality or better signal strength while performing an ECG measurement in parallel, or the signals of the two groups GR1, GR2 can be processed in parallel.

FIG. 4B shows a similar example configuration where two sets of photodiodes are arranged in two groups GR1, GR2 and arranged in a cross shape. For example, the photodiodes of one of the groups are provided with a green wavelength filter while the photodiodes of the other group are provide with a wavelength filter for red/infrared light, such that both PPG and oxygen saturation determination, e.g. for peripheral oxygen saturation $SpO_2$, is possible.

The second selection unit may comprise further voltage inputs that could be selected with the second selection signal as an output voltage to be provided to the voltage ADC. For example, further sensor inputs may exist and/or internal voltages of the signal processing device could be measured.

It will be appreciated that the disclosure is not limited to the disclosed embodiments and to what has been particularly shown and described hereinabove. Rather, features recited in separate dependent claims or in the description may advantageously be combined. Furthermore, the scope of the disclosure includes those variations and modifications, which will be apparent to those skilled in the art and fall within the spirit of the appended claims. The term "comprising", insofar it was used in the claims or in the description, does not exclude other elements or steps of a corresponding feature or procedure. In case that the terms "a" or "an" were used in conjunction with features, they do not exclude a plurality of such features. Moreover, any reference signs in the claims should not be construed as limiting the scope.

The invention claimed is:

1. A signal processing circuit comprising
    a first current sensor input for receiving a first sensor current;

a second current sensor input for receiving a second sensor current;

a voltage sensor input for receiving a sensor voltage;

a first selection unit comprising a first current input, which is coupled to the first current sensor input, and a second current input, which is coupled to the second current sensor input and being configured to, based on a first selection signal, select one of the first and the second current input as a first selected input to be connected to a first current output, and to select one, in particular another one, of the first and the second current input as a second selected input to be connected to a second current output;

a second selection unit comprising a first voltage input, which is coupled to the voltage sensor input and a second voltage input and being configured to, based on a second selection signal, connect one of the first and the second voltage input to a voltage output;

a current analog-digital converter (ADC), coupled to the first current output;

a voltage ADC coupled to the voltage output;

a digital processing block coupled to respective outputs of the current ADC and the voltage ADC; and a current-voltage converter coupled between the second current output and the second voltage input.

2. The signal processing circuit according to claim 1, wherein the first selection unit is configured to simultaneously provide respective currents from the first selected input to the first current output and from the second selected input to the second current output.

3. The signal processing circuit according to claim 1, wherein at least one of the current ADC and the voltage ADC comprises a delta-sigma-modulator.

4. The signal processing circuit according to claim 1, wherein the current-voltage converter comprises a transimpedance amplifier.

5. The signal processing circuit according to claim 1, further comprising at least one offset current source connected to the first current output or to the second current output.

6. The signal processing circuit according to claim 1, wherein the digital processing block comprises a buffer element for buffering digital values provided by the current ADC and the voltage ADC.

7. The signal processing circuit according to claim 1, further comprising at least one further current sensor input for receiving at least one further sensor current, wherein the first selection unit is configured to, based on the first selection signal, select one of the first, the second and the at least one further current input as the first selected input and to select one, in particular another one, of the first, the second and the at least one further current input as the second selected input.

8. A signal processing device comprising
a signal processing circuit according to claim 1;
a first photosensitive element connected to the first current sensor input;
a second photosensitive element connected to the second current sensor input; and
a sensor element connected to the voltage sensor input for providing at least one sensor voltage.

9. The signal processing device according to claim 8, wherein the sensor element comprises at least two electrodes for electrocardiogram, ECG, measurement and wherein the signal processing device further comprises a processing block connected between the voltage sensor input and the first voltage input.

10. The signal processing device according to claim 8, wherein the first and the second photosensitive element are adapted for at least one of the following configurations:
the first and the second photosensitive element are configured for photoplethysmography (PPG);
the first photosensitive element is configured for PPG and the second photosensitive element is configured for detection of oxygen saturation, in particular peripheral oxygen saturation $SpO_2$; and
the first photosensitive element is configured for PPG and the second photosensitive element is configured for ambient light detection.

11. The signal processing device according to claim 8, the signal processing device is implemented as one of the following:
a wearable device;
a smartwatch;
a wristband;
glasses; or
a sensor patch.

* * * * *